United States Patent
Glassman et al.

(10) Patent No.: US 8,153,420 B2
(45) Date of Patent: Apr. 10, 2012

(54) POLYNUCLEOTIDES ENCODING STOP CODONS IN MULTIPLE READING FRAMES AND METHODS OF USE

(75) Inventors: Kimberly E Glassman, Ankeny, IA (US); Shane E Abbitt, Ankeny, IA (US); Karri Klein, Des Moines, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 444 days.

(21) Appl. No.: 12/183,135

(22) Filed: Jul. 31, 2008

(65) Prior Publication Data

US 2009/0038034 A1    Feb. 5, 2009

Related U.S. Application Data

(60) Provisional application No. 60/953,698, filed on Aug. 3, 2007.

(51) Int. Cl.
*C12N 15/09* (2006.01)
*C12N 15/63* (2006.01)
*C12N 15/82* (2006.01)

(52) U.S. Cl. ............ 435/320.1; 435/468; 435/469; 536/23.1; 536/24.2; 800/278

(58) Field of Classification Search ............... None
See application file for complete search history.

(56) References Cited

U.S. PATENT DOCUMENTS

| | | | | |
|---|---|---|---|---|
| 6,271,362 | B1 * | 8/2001 | Morikawa et al. | 536/23.5 |
| 7,754,944 | B2 * | 7/2010 | Fu et al. | 800/294 |
| 2004/0268442 | A1 * | 12/2004 | Miller et al. | 800/288 |
| 2006/0041955 | A1 * | 2/2006 | Godwin et al. | 800/279 |

OTHER PUBLICATIONS

Matthias et al., NAR, 1989, vol. 17, p. 6418.*

* cited by examiner

*Primary Examiner* — Eileen B O Hara
(74) *Attorney, Agent, or Firm* — Pioneer Hi-Bred Int'l, Inc.

(57) ABSTRACT

Compositions having polynucleotides encoding multiple translational stop signals in more than one reading frame are provided. The compositions include isolated polynucleotides, expression cassettes, and vectors, as well as host cells, prokaryotic organisms, and eukaryotic organisms comprising the polynucleotide(s). Methods include using the polynucleotides to stop translation of an mRNA into a protein, to produce a transformed cell and/or organism comprising the polynucleotide, and to identify transformed cells or organisms of a specific lineage.

2 Claims, 1 Drawing Sheet

A. SEQ ID NO: 1
TAAGTGACTAGGGTCACGTGACCCTAGTCACTTA
ATTCACTGATCCCAGTGCACTGGGATCAGTGAAT

B. SEQ ID NO: 2
CTAGCTAGTTAG
GATCGATCAATC

C. SEQ ID NO: 3
CTAACTAACTAA
GATTGATTGATT

D. SEQ ID NO: 4
CTGATCACTAGTTACTTATAG
GACTAGTGATCAATGAATATC

E. SEQ ID NO: 5
TAGTCACTGATTAGTCA
ATCAGTGACTAATCAGT

F. SEQ ID NO: 6
TGACGTGTAAGCCGTAGTTACCTAGTCA
ACTGCACATTCGGCATCAATGGATCAGT

G. SEQ ID NO: 7
CTAACTAACTAG
GATTGATTGATC

POLYNUCLEOTIDES ENCODING STOP CODONS IN MULTIPLE READING FRAMES AND METHODS OF USE

CROSS-REFERENCE TO RELATED APPLICATIONS

This application claims the benefit of U.S. Application Ser. No. 60/953,698 filed Aug. 3, 2007, which is herein incorporated by reference in its entirety.

FIELD OF THE INVENTION

The present invention relates to molecular biology and gene expression.

BACKGROUND

During transcription, transcript termination may not take place exactly at the termination signal at a low, yet significant frequency. Incomplete and/or inaccurate transcription termination may produce messenger RNA (mRNA) transcripts with additional nucleotides containing open reading frames (ORFs) that may be translated to produce unintended proteins. During the production of transgenic cells and organisms, random insertion of the polynucleotide of interest may produce spurious open reading frames (ORFs) at the insertion locus, which may produce an unintended protein product. Various oversight agencies may have regulatory concerns regarding any unintended protein products. Researchers and companies strive to develop and select transgenic organisms products that do not produce or contain unintended products. Therefore, there is a need for compositions and methods to better control, eliminate, and/or minimize the production and/or accumulation of any unintended protein(s) in a transgenic organism.

SUMMARY

Compositions having polynucleotides encoding multiple translational stop signals in more than one reading frame are provided. The compositions include isolated polynucleotides, expression cassettes, and vectors, as well as host cells, prokaryotic organisms, and eukaryotic organisms comprising the polynucleotide(s). Methods include using the polynucleotides to stop translation of an mRNA into a protein, to produce a transformed cell and/or organism comprising the polynucleotide, and to identify transformed cells or organisms of a specific lineage.

BRIEF DESCRIPTION OF FIGURES

FIG. 1. Several examples of ALLSTOPS polynucleotides are shown having stop codons in all six reading frames. The stop codons are shown in bold text.

DETAILED DESCRIPTION

The present invention now will be described more fully hereinafter with reference to the accompanying examples, in which some, but not all of the possible variations encompassed by the teachings are shown. This invention may be embodied in different forms and should not be construed as limited solely to the variations set forth herein to satisfy applicable legal requirements. Modifications and variations could be envisioned by one of skill in art, and are therefore included within the scope of the appended claims. The disclosure of each reference set forth herein is incorporated by reference in its entirety. Although specific terms are employed within, they are used in a generic and descriptive sense only and not for purposes of limitation. The articles "a" and "an" as used herein to refer to at least one, for example "an element" means at least one of the element.

Isolated polynucleotides encoding stop codons in multiple reading frames (ALLSTOPS) are provided. In some examples the isolated polynucleotides encode stop codons in all reading frames in one orientation of a transcript. In some examples the isolated polynucleotides encode stop codons in at least one reading frame in both possible transcript orientations. In some examples the isolated polynucleotides encode stop codons in all six possible reading frames of a transcript. In some examples the ALLSTOPS polynucleotide is at least 12 nucleotides long. In some examples the ALLSTOPS polynucleotide is at least 12 nucleotides to about 450 nucleotides long. In some examples the ALLSTOPS polynucleotide does not encode a functional polypeptide. In some examples the ALLSTOPS polynucleotide is a polynucleotide substantially similar to a polynucleotide of SEQ ID NOs: 1-7. In some examples the ALLSTOPS polynucleotide comprises a functional fragment of a polynucleotide of SEQ ID NOs: 1-7, which retains the encoded stop codons. In some examples the ALLSTOPS polynucleotide is a polynucleotide comprising SEQ ID NOs: 1-7. In some examples the isolated polynucleotide comprises more than one ALLSTOPS polynucleotide. In some examples the isolated polynucleotide comprises more than one ALLSTOPS polynucleotide, wherein at least one ALLSTOPS polynucleotide is substantially similar to any one of SEQ ID NOs: 1-7. In some examples the isolated polynucleotide comprises more than one ALLSTOPS polynucleotide, wherein at least one ALLSTOPS polynucleotide encoding is any one of SEQ ID NOs: 1-7.

Expression cassettes, DNA constructs, and vectors comprising at least one ALLSTOPS polynucleotide are provided. In some examples, the expression cassette, DNA construct, or vector is a T-DNA. In some examples, the expression cassette, DNA construct, or vector is a viral DNA, including a viral replicon. In some examples, the expression cassette, DNA construct, or vector further comprises a polynucleotide of interest (POI). In some examples the polynucleotide of interest is operably linked to at least one ALLSTOPS polynucleotide. In some examples the polynucleotide of interest is operably linked to at least one promoter (PRO) functional in a host cell. In some examples the polynucleotide of interest is operably linked to at least one promoter and further operably linked to at least one ALLSTOPS polynucleotide. In some examples a polynucleotide of interest is operably linked on both sides to an ALLSTOPS polynucleotide. In some examples, the expression cassette, DNA construct, or vector further comprises more than one polynucleotide of interest, wherein each polynucleotide of interest is optionally operably linked to a promoter. When the expression cassette, DNA construct, or vector comprises more than one polynucleotide if interest, an ALLSTOPS polynucleotide can be positioned outside of all polynucleotides of interest, between polynucleotides of interest, or between only select pairs or clusters of polynucleotides of interest, or any combination thereof. Numerous configurations are possible, including but not limited to examples such as: ALLSTOPS::POI1-POI2; ALLSTOPS::POI1-POI2::ALLSTOPS; ALLSTOPS::PRO1::POI1-POI2; ALLSTOPS::PRO1::POI1-POI2::ALLSTOPS; ALLSTOPS::POI1-PRO2::POI2; ALLSTOPS::POI1-PRO2::POI2::ALLSTOPS; ALLSTOPS::PRO1::POI1-PRO2::POI2; ALLSTOPS::PRO1::POI1-PRO2::POI2::ALLSTOPS; ALLSTOPS::POI1-POI2::PRO2;

ALLSTOPS::POI1-POI2::PRO2::ALLSTOPS; ALLSTOPS::POI1::ALLSTOPS-POI2; ALLSTOPS::POI1::ALLSTOPS::POI2::ALLSTOPS; or combinations thereof.

Expression cassettes, DNA constructs, and vectors comprising at least one ALLSTOPS polynucleotide may optionally comprise other polynucleotides including screenable markers, promoters, enhancers, terminators, untranslated regions, insulators, multiple cloning sites, restriction sites, homing endonuclease sites, recombination sites, transposition sequences, linkers, adapters, other sequences, or any combination thereof.

Host cells comprising at least one ALLSTOPS polynucleotide are provided. Host cells include prokaryotes, viruses, and eukaryotes. Prokaryotes include bacteria such as *E. coli* or *Agrobacterium*, including bacteria used to propagate, amplify, express and/or transfer polynucleotides to another host. Viruses include phage, plant viruses, avian viruses, and mammalian viruses, including viruses used to propagate, amplify, express and/or transfer polynucleotides to another host. Eukaryotes include yeast, fungi, plants, and animal cells. Host organisms comprising a host cell having an ALLSTOPS polynucleotide are also provided. In some examples the host cell is a plant cell. In some examples the plant cell is from a monocot, including but not limited to maize, barley, wheat, oat, rye, millet, sorghum, rice, switchgrass or turfgrass. In some examples the plant cell is from a dicot, including but not limited to soy, *Brassica*, alfalfa, *Arabidopsis*, tobacco, sunflower, or safflower. Seeds comprising an ALLSTOPS polynucleotide are also provided.

Methods using the isolated ALLSTOPS polynucleotide compositions are provided. Methods include using the isolated polynucleotides to produce a transformed host cell having the polynucleotide inserted into its genome. The ALLSTOPS polynucleotide may be inserted into a nuclear, organellar, and/or plastidic genome. In some examples, insertion of an ALLSTOPS polynucleotide into a host genome truncates translation of any unintended mRNA transcript. In some examples, insertion of an ALLSTOPS polynucleotide into a host genome stimulates degradation of any unintended mRNA transcript. In some examples, insertion of an ALLSTOPS polynucleotide into a host genome provides a means to identify transformed cells, organisms, and any progeny derived from the transformed host cell. In some examples, the progeny comprise a proprietary germplasm or derivative thereof. Any host cell can be used in the methods, including but not limited to bacterial cells, viruses, plant cells, and mammalian cells. In some examples the host cell is a bacterial cell, including but not limited to *E. coli* or *Agrobacterium*. In some examples the host cell is a plant cell. In some examples the plant cell is from a monocot, including but not limited to maize, barley, wheat, oat, rye, millet, sorghum, rice, switchgrass or turfgrass. In some examples the plant cell is from a dicot, including but not limited to soy, *Brassica*, alfalfa, *Arabidopsis*, tobacco, sunflower, or safflower.

Transcriptional termination in eukaryotes is heterogeneous and the termination sequences are not well-characterized. Additionally, unintended ORFs may occur due to the random integration of the transgenic insertion into the genome of an organism. For example, if insertion occurs in the middle of an endogenous gene, the promoter from the endogenous gene could theoretically initiate transcription from outside the transgenic insert and transcribe into the transgenic insert generating an unintended transcript potentially containing an unintended ORF. In some instances, some rearrangement and or partial duplication of the transgene insert may occur, which may produce an ORF initiating within the insert, which may extend into flanking genomic sequence.

Termination of protein biosynthesis occurs when the ribosome reaches a stop codon, for which there is no tRNA. At this point, protein biosynthesis halts and a release factor binds to the stop codon. Binding of the release factor induces a nucleophilic attack of the C-terminus of the nascent peptide by water, and hydrolytic release of the peptide from the ribosome. The ribosome, release factor, and uncharged tRNA dissociate and translation is complete. All three stop codons, UAA, UAG, and UGA, function in all living organisms. A single stop codon in the proper reading frame is sufficient to halt translation. Providing a single stop codon in the correct frame and orientation would halt translation of an unintended ORF. Therefore, even if an unintended mRNA transcript is made, the production of an unintended protein is stopped or minimized. Given the random nature of possible unintended ORFs, the correct frame and orientation of the ORF is not readily predictable, therefore providing stop codons in multiple reading frames and optionally orientations assures terminating translation of spurious transcripts. The combination of stop codons allows ALLSTOPS to be a translational termination sequence capable of functioning in any reading frame. When ALLSTOPS is positioned downstream (3') of any ORF, translation will be halted at the ALLSTOPS sequence.

In addition to stopping translation, ALLSTOPS can be used to identify transformed cells or organisms. ALLSTOPS can be incorporated into every transformed cell or organism generated and can be used to identify transgenic events, proprietary germplasm, progeny, and/or adventitious presence. Organisms can be analyzed to determine the presence or absence of ALLSTOPS using standard methods including but not limited to Southern blots (Southern (1975) *Mol Biol* 98:503-517), Northern blots, polymerase chain reaction (PCR and/or rtPCR) analyses, genomic sequencing, protein profile comparisons, or any combination thereof.

A polynucleotide is any nucleic acid molecule comprising naturally occurring, synthetic, modified ribonucleotides, and/or modified deoxyribonucleotides, and combinations thereof. Polynucleotides encompass all structural forms of sequences including, but not limited to, single-stranded, double-stranded, multi-stranded, linear, circular, branched, hairpins, stem-loop structures, and the like.

ALLSTOPS polynucleotides include fragments and variants that retain the function of the ALLSTOPS polynucleotides disclosed herein. A fragment is a portion of the sequence which retains at least one function of the original or reference sequence. Fragments of a polynucleotide sequence includes sequences which range from at least 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 100, 150, 200, 250, 300, 350, 400, 450 nucleotides or longer. A variant sequence is a substantially similar sequence which retains at least one function of the original or reference sequence. For polynucleotides, a variant encompasses deletion, addition, and/or substitution of one or more nucleotides at one or more sites as compared to the original polynucleotide. For polypeptides, a variant encompasses deletion, addition, and/or substitution of one or more amino acids at one or more sites as compared to the original polypeptide. Variants include sequences derived from an original sequence. A substantially similar sequence, when aligned with an ALLSTOPS sequence, has a significant number of nucleotides in common and retains the stop codons in multiple reading frames. Alternative stop codons may be substituted, intervening nucleotides added, deleted, or substituted, or nucleotides deleted or added to either end of the molecule as long as the resulting polynucleotide retains stop codons in the multiple reading frames. Any nucleotide can be substituted adjacent to or between stop codons, as long as the stop codons and reading frames are maintained. Due to the nature of ALLSTOPS polynucleotides, substantially similar sequences encompass sequences having a low percent sequence identity as compared to an ALLSTOPS sequence, but these substantially similar sequences are readily identifiable by the number of stop codons in multiple reading frames.

A DNA construct comprises an ALLSTOPS polynucleotide provided herein. An expression cassette, or recombinant expression cassette, comprises a polynucleotide which, when present in the genome of an organism, is heterologous or foreign to that chromosomal location in the host genome, wherein at least a portion of the expression cassette can provide or produce at least one RNA. DNA constructs and expression cassette may be produced using standard methods, see, for example, Sambrook, et al., (1989) *Molecular Cloning: A Laboratory Manual,* 2nd Edition, Cold Spring Harbor Laboratory Press, Cold Spring Harbor, N.Y.; and Glover (eds.) (1985) *DNA Cloning: A Practical Approach,* Volumes I and II. In preparing the expression cassette or DNA construct, various fragments may be manipulated to provide the sequences in a proper orientation and/or in the proper reading frame. Adapters or linkers may be employed to join the fragments. Other manipulations may be used to provide convenient restriction sites, remove of superfluous DNA, or remove of restriction sites. For example, in vitro mutagenesis, primer repair, restriction, annealing, resubstitutions, transitions, transversions, or recombination systems may be used.

Regulatory regions, including promoters, transcriptional regulatory regions, and/or translational termination regions, may be endogenous to the host cell, genomic location, and/or to each other. Alternatively, the regulatory regions may be heterologous to the host cell, genomic location, and/or to each other. A heterologous sequence is a sequence that originates from a foreign species, or, if from the same species, is substantially modified from its native form in composition and/or genomic locus by deliberate human intervention. An expression cassette may include 5' and 3' regulatory sequences operably linked to a polynucleotide of interest, which is operably linked to an ALLSTOPS polynucleotide. The ALLSTOPS polynucleotide may also be outside of the expression cassette but still operably linked. Operably linked elements may be contiguous or non-contiguous. The expression cassette may additionally contain at least one additional polynucleotide of interest to be introduced into the organism. One or more expression cassettes may be linked together as one transcriptional unit. In an *Agrobacterium* vector for transformation of a plant cell, multiple expression cassettes may be located in one transcriptional unit between the left and right borders of the T-DNA vector. Alternatively, polynucleotide(s) of interest can be provided on separate DNA constructs or expression cassettes. A DNA construct or expression cassette may optionally contain a screenable marker.

The ALLSTOPS sequence may be positioned almost anywhere within a DNA construct. For example, the ALLSTOPS sequence could be positioned 3' to the transcriptional termination sequence, the translational termination sequence, or to the polynucleotide of interest. The ALLSTOPS sequence may also be located 5' or 3' to an expression cassette. Another option is to place ALLSTOPS flanking both ends of the DNA construct. Multiple ALLSTOPS sequences may be used within and/or outside of the expression cassette. For example, the ALLSTOPS sequence could be placed between each expression cassette within a transcriptional unit. Alternatively, ALLSTOPS could be places 5' and 3' to the expression cassette, in order to prevent aberrant translation into the expression cassette or out of the expression cassette. An ALLSTOPS sequence could be placed either 3' or 5' to the left border and an ALLSTOPS could be placed either 3' or 5' to the right border in a T-DNA vector.

Any promoter, or combination of promoters, can be used. Promoters are typically selected based on the desired expression profile. A promoter is a region of DNA involved in recognition and binding of RNA polymerase and other proteins to initiate transcription. A plant promoter is a promoter capable of initiating transcription in a plant cell, for a review of plant promoters see, Potenza, et al., (2004) *In Vitro Cell Dev Biol* 40:1-22.

Constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313: 810-812); rice actin (McElroy, et al., (1990) *Plant Cell* 2:163-171); ubiquitin (Christensen, et al., (1989) *Plant Mol Biol* 12:619-632 and Christensen, et al., (1992) *Plant Mol Biol* 18:675-689); PEMU (Last, et al., (1991) *Theor Appl Genet* 81:581-588); MAS (Velten, et al., (1984) *EMBO J* 3:2723-2730); ALS promoter (U.S. Pat. No. 5,659,026), and the like. Other constitutive promoters are described, for example, in U.S. Pat. Nos. 5,608,149; 5,608,144; 5,604,121; 5,569,597; 5,466,785; 5,399,680; 5,268,463; 5,608,142 and 6,177,611.

In some examples an inducible promoter may be used. Pathogen-inducible promoters induced following infection by a pathogen include, but are not limited to those regulating expression of PR proteins, SAR proteins, beta-1,3-glucanase, chitinase, etc. See, for example, Redolfi, et al., (1983) *Neth J Plant Pathol* 89:245-254; Uknes, et al., (1992) *Plant Cell* 4:645-656; Van Loon (1985) *Plant Mol Virol* 4:111-116; WO 99/43819; Marineau, et al., (1987) *Plant Mol Biol* 9:335-342; Matton, et al., (1989) *Mol Plant-Microbe Interact* 2:325-331; Somsisch, et al., (1986) *Proc Natl Acad Sci USA* 83:2427-2430; Somsisch, et al., (1988) *Mol Gen Genet* 2:93-98; Yang (1996) *Proc Natl Acad Sci USA* 93:14972-14977; Chen, et al., (1996) *Plant J* 10:955-966; Zhang, et al., (1994) *Proc Natl Acad Sci USA* 91:2507-2511; Warner, et al., (1993) *Plant J* 3:191-201; Siebertz, et al., (1989) *Plant Cell* 1:961-968; U.S. Pat. No. 5,750,386 (nematode-inducible); and the references cited therein; and Cordero, et al., (1992) *Physiol Mol Plant Path* 41:189-200 (*Fusarium*-inducible). Wound-inducible promoters include potato proteinase inhibitor (pin II) gene (Ryan (1990) *Ann Rev Phytopath* 28:425-449; Duan, et al., (1996) *Nat Biotechnol* 14:494-498); wun1 and wun2 (U.S. Pat. No. 5,428,148); win1 and win2 (Stanford, et al., (1989) *Mol Gen Genet* 215:200-208); systemin (McGurl, et al., (1992) *Science* 225:1570-1573); WIP1 (Rohmeier, et al., (1993) *Plant Mol Biol* 22:783-792; Eckelkamp, et al., (1993) *FEBS Lett* 323:73-76); MPI gene (Corderok, et al., (1994) *Plant J* 6:141-150); and the like.

Chemical-regulated promoters can be used to modulate the expression of a gene through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzenesulfonamide herbicide safeners (De Veylder, et al., (1997) *Plant Cell Physiol* 38:568-77), the maize GST promoter (GST-II-27, WO 93/01294), activated by hydrophobic electrophilic compounds used as pre-emergent herbicides, and the tobacco PR-1a promoter (Ono, et al., (2004) *Biosci Biotechnol Biochem* 68:803-7) activated by salicylic acid. Other chemical-regulated promoters of interest include steroid-responsive promoters (see, for example, the glucocorticoid-inducible promoter in Schena, et al., (1991) *Proc Natl Acad Sci USA* 88:10421-10425; and McNellis, et al., (1998) *Plant J* 14:247-257); tetracycline-inducible and tetracycline-repressible promoters (Gatz, et al., (1991) *Mol Gen Genet* 227:229-237; U.S. Pat. Nos. 5,814,618 and 5,789,156).

Tissue-preferred promoters can be utilized to target enhanced expression of a sequence of interest within a particular plant tissue. Tissue-preferred promoters include Kawamata, et al., (1997) *Plant Cell Physiol* 38:792-803; Hansen, et al., (1997) *Mol Gen Genet* 254:337-343; Russell, et al., (1997) *Transgenic Res* 6:157-168; Rinehart, et al., (1996) *Plant Physiol* 112:1331-1341; Van Camp, et al., (1996) *Plant Physiol* 112:525-535; Canevascini, et al., (1996) *Plant Physiol* 112:513-524; Lam (1994) *Results Probl Cell Differ* 20:181-196; and Guevara-Garcia, et al., (1993) *Plant J* 4:495-505. Leaf-preferred promoters include, for example, Yamamoto, et al., (1997) *Plant J* 12:255-265; Kwon, et al., (1994) *Plant Physiol* 105:357-67; Yamamoto, et al., (1994) *Plant Cell Physiol* 35:773-778; Gotor, et al., (1993) *Plant J* 3:509-18; Orozco, et al., (1993) *Plant Mol Biol* 23:1129-1138; Matsuoka, et al., (1993) *Proc Natl Acad Sci USA* 90(20):9586-9590; cab and rubisco promoters (Simpson, et al., (1958) *EMBO J* 4:2723-2729; Timko, et al., (1988) *Nature* 318:57-58). Root-preferred promoters are known and include, for example, Hire, et al., (1992) *Plant Mol Biol* 20:207-218 (soybean root-specific glutamine synthase gene); Miao, et al., (1991) *Plant Cell* 3:11-22 (cytosolic glutamine synthase (GS) expressed in roots and root nodules of soybean; Keller and Baumgartner (1991) *Plant Cell* 3:1051-1061 (root-specific control element in the GRP 1.8 gene of French bean); Sanger, et al., (1990) *Plant Mol Biol* 14:433-443 (root-specific promoter of *A. tumefaciens* mannopine synthase (MAS)); Bogusz, et al., (1990) *Plant Cell* 2:633-641 (root-specific promoters isolated from *Parasponia andersonii* and *Trema tomentosa*); Leach and Aoyagi (1991) *Plant Sci* 79:69-76 (*A. rhizogenes* roIC and roID root-inducing genes); Teeri, et al., (1989) *EMBO J* 8:343-350 (*Agrobacterium* wound-induced TR1' and TR2' genes); VfENOD-GRP3 gene promoter (Kuster, et al., (1995) *Plant Mol Biol* 29:759-772); and roIB promoter (Capana, et al., (1994) *Plant Mol Biol* 25(4):681-691; phaseolin gene (Murai, et al., (1983) *Science* 23:476-482; Sengopta-Gopalen, et al., (1988) *Proc Natl Acad Sci USA* 82:3320-3324). See also, U.S. Pat. Nos. 5,837,876; 5,750,386; 5,633,363; 5,459,252; 5,401,836; 5,110,732 and 5,023,179. Seed-preferred promoters include both seed-specific promoters active during seed development, as well as seed-germinating promoters active during seed germination. See, Thompson, et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (see, WO 00/11177 and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO 00/12733, where seed-preferred promoters from end1 and end2 genes are disclosed.

Commonly used prokaryotic control sequences include promoters for transcription initiation, optionally with an operator, along with ribosome binding sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res* 8:4057) and the lambda derived P L promoter and N-gene ribosome binding site (Shimatake, et al., (1981) *Nature* 292:128).

The expression cassettes may additionally contain 5' leader sequences. Such leader sequences can act to enhance translation. Translation leaders include picornavirus leaders, for example, EMCV leader (Encephalomyocarditis 5' noncoding region) (Elroy-Stein, et al., (1989) *Proc Natl Acad Sci USA* 86:6126-6130); polyvirus leaders, for example, TEV leader (Tobacco Etch Virus) (Gallie, et al., (1995) *Gene* 165:233-238), MDMV leader (Maize Dwarf Mosaic Virus) (Allison, et al., (1986) *Virology* 154:9-20; Kong, et al., (1988) *Arch Virol* 143:1791-1799), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, N.Y.), pp. 237-256); and maize chlorotic mottle virus leader (MCMV) (Lommel, et al., (1991) *Virology* 81:382-385). See also, Della-Cioppa, et al., (1987) *Plant Physiol* 84:965-968. Other methods or sequences, including introns, known to enhance translation can also be utilized alone or in combination with any of the 5' leader sequences above.

Convenient transcriptional termination regions are available from the Ti-plasmid of *A. tumefaciens*, such as the octopine synthase and nopaline synthase (nos) termination regions. See also, Guerineau, et al., (1991) *Mol Gen Genet* 262:141-144; Proudfoot (1991) *Cell* 64:671-674; Sanfacon, et al., (1991) *Genes Dev* 5:141-149; Mogen, et al., (1990) *Plant Cell* 2:1261-1272; Munroe, et al., (1990) *Gene* 91:151-158; Ballas, et al., (1989) *Nucleic Acids Res* 17:7891-7903; and Joshi, et al., (1987) *Nucleic Acids Res* 15:9627-9639.

A vector is selected to allow introduction into the appropriate host cell. An expression cassette may be incorporated into a variety of vectors. Vectors include circular or linear polynucleotides and can be derived from chromosomal, episomal, and virus-derived vectors, including, mini-chromosomes, artificial chromosomes, satellite chromosomes and the like; vectors derived from bacterial plasmids, from bacteriophage, from yeast episomes, from yeast chromosomal elements, including yeast artificial chromosomes; from viruses, such as, baculoviruses, papovaviruses, such as, SV40, Vaccinia viruses, adenoviruses, poxviruses, pseudorabies viruses, retroviruses and plant viruses. Vectors may also be derived from combinations of these sources such as those derived from plasmid and bacteriophage genetic elements, e.g. cosmids and phagemids.

Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Prokaryotic/bacterial expression systems for expressing a protein are available using *Bacillus* sp. and *Salmonella* (Palva, et al., (1983) *Gene* 22:229-235; Mosbach, et al., (1983) *Nature* 302:543-545). The Tet operon and the Lac operon can be used.

Two widely utilized yeasts for production of eukaryotic proteins are *Saccharomyces cerevisiae* and *Pichia pastoris*. Vectors, strains, and protocols for expression in *Saccharomyces* and *Pichia* are known and available from commercial suppliers (e.g., InVitrogen). Suitable vectors usually have expression control sequences, such as promoters, including 3-phosphoglycerate kinase or alcohol oxidase, and an origin of replication, termination sequences and the like as desired. Examples of vectors for expression in yeast include pYepSec1 (Baldari, et al., (1987) *EMBO J* 6:229-234); pMFa (Kurjan, et al., (1982) *Cell* 30:933-943); and pJRY88 (Schultz, et al., (1987) *Gene* 54:113-123).

Polynucleotides can be expressed in insect cells using, for example, baculovirus expression vectors. Baculovirus vectors available for expression of proteins in cultured insect cells, such as, Sf9 cells, include the pAc series (Smith, et al., (1983) *Mol. Cell Biol* 3:2156-2165) and the pVL series (Lucklow, et al., (1989) *Virology* 170:31-39). Established protocols with vectors and reagents are available from commercial suppliers (e.g., InVitrogen, Life Technologies Inc). Commercial vectors are available with various promoters, such as polyhedrin and p10, optional signal sequences for protein secretion, or affinity tags, such as 6× histidine. These recombinant viruses are grown, maintained and propagated in commercially available cell lines derived from several insect species including *Spodoptera frugiperda* and *Trichoplusia ni*. The insect cells can be cultured using well-established protocols in a variety of different media, for example, with and without bovine serum supplementation. The cultured cells are infected with the recombinant viruses and the sequence-of-interest is expressed. Proteins expressed with the baculovirus system have been extensively characterized and, in many cases, their post-translational modifications such as phosphorylation, acylation, etc., are identical to the natively expressed protein.

Polynucleotides may be expressed in mammalian cells using mammalian expression vectors. Examples of mammalian expression vectors include pCDM8 (Seed (1987) *Nature* 329:840) and pMT2PC (Kaufman, et. al., (1987) *EMBO J* 6:187-195).

DNA constructs can also comprise a screenable marker gene for the identification and/or selection of transformed cells. Screenable marker genes can be used to identify and/or select transformed cells or tissues. Marker genes include genes encoding antibiotic resistance, such as those encoding spectinomycin, ampicillin, kanamycin, tetracycline, Basta, neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Polynucleotides which encode products which are otherwise lacking in the cell can also be used as markers, including for example, tRNA genes, and auxotrophic markers. Additional markers include phenotypic markers such as β-galactosidase, GUS, and fluorescent proteins such as green fluorescent protein (GFP) (Su, et al., (2004) *Biotechnol Bioeng* 85:610-9; Fetter, et al., (2004) *Plant Cell* 16:215-28), cyan fluorescent protein (CFP) (Bolte, et al., (2004) *J Cell Science* 117:943-54; Kato, et al., (2002) *Plant Physiol* 129:913-42), yellow fluorescent protein (YFP) (Bolte, et al., (2004) *J Cell Science* 117:943-54), and red fluorescent protein (RFP). Additional markers are available, see for example Yarranton (1992) *Curr Opin Biotech* 3:506-511; Christopherson, et al., (1992) *Proc Natl Acad Sci USA* 89:6314-6318; Yao, et al., (1992) *Cell* 71:63-72; Reznikoff (1992) *Mol Microbiol* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc Natl Acad Sci USA* 86:5400-5404; Fuerst, et al., (1989) *Proc Natl Acad Sci USA* 86:2549-2553; Deuschle, et al., (1990) *Science* 248:480-483; Gossen (1993) Ph.D. Thesis, University of Heidelberg; Reines, et al., (1993) *Proc Natl Acad Sci USA* 90:1917-1921; Labow, et al., (1990) *Mol Cell Biol* 10:3343-3356; Zambretti, et al., (1992) *Proc Natl Acad Sci USA* 89:3952-3956; Baim, et al., (1991) *Proc Natl Acad Sci USA* 88:5072-5076; Wyborski, et al., (1991) *Nucleic Acids Res* 19:4647-4653; Hillenand-Wissman (1989) *Topics Mol Struc Biol* 10:143-162; Degenkolb, et al., (1991) *Antimicrob Agents Chemother* 35:1591-1595; Kleinschnidt, et al., (1988) *Biochemistry* 27:1094-1104; Bonin (1993) Ph.D. Thesis, University of Heidelberg; Gossen, et al, (1992) *Proc Natl Acad Sci USA* 89:5547-5551; Oliva, et al., (1992) *Antimicrob Agents Chemother* 36:913-919; Hlavka, et al., (1985) Handbook of Experimental Pharmacology, Vol. 78 (Springer-Verlag, Berlin); Gill, et al., (1988) *Nature* 334:721-724.

The methods herein involve introducing a polynucleotide encoding an ALLSTOPS into a cell, tissue, or organism. Introducing encompasses any means of presenting a composition to an organism in such a manner that the composition gains access to the interior of a cell of the organism. Compositions included polynucleotides, polypeptides, carriers, other reagents, or combinations thereof. These methods do not depend on a particular method for introducing a sequence into an organism, only that the polynucleotide or polypeptides gains access to the interior of at least one cell of the organism.

Transformed host cells are prepared by introducing a DNA construct into the cells using standard techniques. Methods for introducing polynucleotide or polypeptides into organisms are known, including, but not limited to, stable transformation methods, transient transformation methods, virus-mediated methods and sexual crossing. Stable transformation indicates that the introduced polynucleotide integrates into the genome of the organism and is capable of being inherited by progeny thereof. Transient transformation indicates that the introduced composition is only temporarily expressed or present in the organism. These methods include, but are not limited to, calcium phosphate transfection, DEAE-dextran-mediated transfection, cationic lipid-mediated transfection, electroporation, transduction, infection, lipofection, *Agrobacterium*-mediated transformation, ballistic particle acceleration, and the like.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway, et al., (1986) *Biotechniques* 4:320-334; and U.S. Pat. No. 6,300,543), meristem transformation (U.S. Pat. No. 5,736,369), electroporation (Riggs, et al., (1986) *Proc Natl Acad Sci USA* 83:5602-5606, *Agrobacterium*-mediated transformation (U.S. Pat. Nos. 5,563,055 and 5,981,840), direct gene transfer (Paszkowski, et al., (1984) *EMBO J* 3:2717-2722), and ballistic particle acceleration (U.S. Pat. Nos. 4,945,050; 5,879,918; 5,886,244; 5,932,782; Tomes, et al., (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe, et al., (1988) *Biotechnology* 6:923-926; Weissinger, et al., (1988) *Ann Rev Genet* 22:421-477; Sanford, et al., (1987) *Particulate Science and Technology* 5:27-37 (onion); Christou, et al., (1988) Plant Physiol 87:671-674 (soybean); Finer and McMullen (1991) *In Vitro Cell Dev Biol* 27P:175-182 (soybean); Singh, et al., (1998) *Theor Appl Genet* 96:319-324 (soybean); Datta, et al., (1990) *Biotechnology* 8:736-740 (rice); Klein, et al., (1988) *Proc Natl Acad Sci USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol* 91:440-444 (maize); Fromm, et al., (1990) *Biotechnology* 8:833-839 (maize); Hooykaas-Van Slogteren, et al., (1984) *Nature* 311:763-764; U.S. Pat. No. 5,736,369 (cereals); Bytebier, et al., (1987) *Proc Natl Acad Sci USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Rep* 9:415-418; Kaeppler, et al., (1992) *Theor Appl Genet* 84:560-566 (whisker-mediated transformation); D'Halluin, et al., (1992) *Plant Cell* 4:1495-1505 (electroporation); Li, et al., (1993) *Plant Cell Rep* 12:250-255; Christou and Ford (1995) *Annals of Botany* 75:407-413 (rice); and, Osjoda, et al., (1996) *Nat Biotechnol* 14:745-750 (maize via *Agrobacterium tumefaciens*).

Alternatively, the polynucleotides may be introduced into plants by contacting plants with a virus or viral nucleic acids. Generally, such methods involve incorporating a polynucleotide within a viral DNA or RNA molecule. It is recognized that a polypeptide of interest may be initially synthesized as part of a viral polyprotein, which later may be processed by proteolysis in vivo or in vitro to produce the desired recombinant protein. Useful promoters also encompass promoters utilized for transcription by viral RNA polymerases. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931.

Transient transformation methods include, but are not limited to, the introduction of polypeptides directly into the organism, the introduction of polynucleotides such as DNA and/or RNA polynucleotides, and the introduction of the RNA transcript, such as an mRNA into the organism. Such methods include, for example, microinjection or particle bombardment. See, for example, Crossway, et al., (1986) *Mol Gen Genet* 202:179-185; Nomura, et al., (1986) *Plant Sci* 44:53-58; Hepler, et al., (1994) *Proc Natl Acad Sci USA* 91:2176-2180; and, Hush, et al., (1994) *J Cell Sci* 107:775-784.

The cells having the introduced sequence may be grown into plants in accordance with conventional ways, see, for example, McCormick, et al., (1986) *Plant Cell Rep* 5:81-84. These plants may then be grown, self pollinated, outcrossed, or backcrossed, and the resulting progeny having the polynucleotide and/or trait. Sexual crossing techniques include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. Two or more generations may be grown to ensure that the polynucleotide is stably maintained and inherited, and seeds harvested. In this manner, transformed seed, also referred to as transgenic seed, having a polynucleotide are provided.

ALLSTOPS may be introduced into any cell from any organism. Examples of such target cells include cells derived from vertebrates including mammals, such as, humans, bovine species, ovine species murine species, simian species; fungi; bacteria; insect; plants; and the like. Organisms of interest include, but are not limited to both prokaryotic and eukaryotic organisms including, for example, bacteria, viruses, yeast, insects, fungi, mammals, and plants. The term plant includes plant cells, plant protoplasts, plant cell tissue cultures from which plants can be regenerated, plant calli, plant clumps, and plant cells that are intact in plants or parts of plants such as embryos, pollen, ovules, seeds, flowers, kernels, ears, cobs, husks, stalks, roots, root tips, anthers, and the like.

ALLSTOPS may be introduced into any plant species, including, but not limited to, monocots and dicots. Examples of plant species of interest include, but are not limited to, corn (*Zea mays*), *Brassica* sp. (e.g., *B. napus, B. rapa, B. juncea*), *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), turfgrass, switchgrass, oats, barley, vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Prokaryotic cells may also be used. Prokaryotes include various strains of *E. coli*; however, other microbial strains may also be used, including, for example, *Bacillus* sp, *Salmonella*, and *Agrobacterium*. Exemplary *Agrobacterium* strains include C58c1 (pGUSINT), Agt121 (pBUSINT), EHA101 (pMTCA23GUSINT), EHA105 (pMT1), LBA4404 (pTOK233), GU2260, BU3600, AGL-1, and LBA4402. Such strains are described in detail in Chan, et al., (1992) *Plant Cell Physiol* 33:577; Smith, et al., (1995) *Crop Sci* 35:301 and Hiei, et al., (1994) *Plant J* 6:271-282. Exemplary bacterial strains include, but are not limited to, C600 (ATCC 23724), C600hfl, DH1 (ATCC 33849), DH5α, DH5αF', ER1727, GM31, GM119 (ATCC 53339), GM2163, HB101 (ATCC 33694), JM83 (ATCC 35607), JM101 (ATCC 33876), JM103 (ATCC 39403), JM105 (ATCC 47016), JM107 (ATCC 47014), JM108, JM109 (ATCC53323), JM110 (ATCC 47013), LE392 (ATCC 33572), K802 (ATCC 33526), NM522 (ATCC 47000), RR1 (ATCC31343), X1997 (ATCC 31244), and Y1088 (ATCC 37195). See also, Jendrisak, et al., (1987) Guide to Molecular Cloning Techniques, Academic Press, 359-371, Hanahan, et al., (1983) *J Mol Biol* 166:557-580, Schatz, et al., (1989) *Cell* 59:1035, Bullock, et al., (1987) *BioTechniques* 5:376-378, ATCC Bacteria and Bacteriophages (1996) 9th Edition, and Palmer, et al., (1994) *Gene* 143:7-8.

Viral strains include, but are not limited to, geminivirus, begomovirus, curtovirus, mastrevirus, (−) strand RNA viruses, (+) strand RNA viruses, potyvirus, potexvirus, tobamovirus, or other DNA viruses, nanoviruses, viroids and the like, for example, African cassava mosaic virus (ACMV) (Ward, et al., (1988) *EMBO J* 7:899-904 and Hayes, et al., (1988) *Nature* 334:179-182), barley stripe mosaic virus (BSM) (Joshi, et al., (1990) *EMBO J* 9:2663-2669), cauliflower mosaic virus (CaMV) (Gronenborn, et al., (1981) *Nature* 294:773-776 and Brisson, et al., (1984) *Nature* 310: 511-514), maize streak virus (MSV) (Lazarowitz, et al., (1989) *EMBO J* 8:1023-1032 and Shen, et al., (1994) *J Gen Virol* 76:965-969), tobacco mosaic virus (TMV) (Takamatsu, et al., (1987) *EMBO J* 6:307-311 and Dawson, et al., (1989) *Virology* 172:285-292), tomato golden mosaic virus (TGMV) (Elmer, et al., (1990) *Nucleic Acids Res* 18:2001-2006), and wheat dwarf virus (WDV) (Woolston, et al., (1989) *Nucleic Acids Res* 17:6029-6041) and derivatives thereof. See also, Porat, et al., (1996) *Mol Biotechnol* 5:209-221.

Example 1

Any method can be used to design a polynucleotide encoding stop codons in multiple reading frames. In this example, the polynucleotides encoding stop codons in multiple reading frames were designed manually. These polynucleotides can optionally be designed to include other elements, such as sequences to facilitate isolation, identification, manipulation, and/or cloning of the polynucleotide or a cell comprising the polynucleotide and include elements such as restriction enzyme recognition sites, homing endonuclease recognition sites, multiple cloning sites, transposition elements, recombination sites, or any combination thereof.

ALLSTOPS polynucleotides were designed by selecting a stop codon, adding one or more nucleotides to shift the reading frame, selecting another stop codon, and repeating these steps until the designed polynucleotide had stop codons in the desired reading frames. Depending on the stop codons selected, double-stranded sequences as short as 12 bp can be designed having stop codons in all 6 possible reading frames.

To produce an ALLSTOPS polynucleotide comprising SEQ ID NO: 1 and having to suitable restriction sites for cloning into a T-DNA target vector RB region, four oligonucleotides for were designed and synthesized (SEQ ID NOS: 8-11). The oligonucleotides were annealed, ligated into linear vectors, and sequenced. A polynucleotide comprising ALLSTOPS sequence (SEQ ID NO: 1) was inserted into a T-DNA vector, approximately 250 bp downstream (3' to) the T-DNA right border (RB) sequence.

To produce an ALLSTOPS polynucleotide comprising SEQ ID NO: 1 and having to suitable restriction sites for cloning into a T-DNA target vector LB region, four oligonucleotides for were designed and synthesized (SEQ ID NOS: 12-15). The oligonucleotides were annealed, ligated into linear vectors, and sequenced. A polynucleotide comprising ALLSTOPS sequence (SEQ ID NO: 1) was inserted into the T-DNA vector, approximately 150 bp upstream (5' to) the T-DNA left border (LB) sequence.

Synthetic oligonucleotides were designed and can be chemically synthesized to generate the double-stranded DNA sequence of SEQ ID NOS: 2-7. The oligonucleotides are annealed, ligated into linear vectors, and sequenced.

In addition, ALLSTOPS sequences can be positioned between gene expression cassettes in stacked gene constructs to interrupt any unintended ORFs arising in one cassette and extending into an adjacent cassette.

Besides including an ALLSTOPS polynucleotide adjacent to or flanking both sides of an expression cassette in a DNA construct, an ALLSTOPS sequence can also be included in the middle of each arm of an inverted repeat silencing cassette, or be included in a DNA construct as an inverted repeat in its own right. Including ALLSTOPS in an inverted repeat structure may serve two purposes. Translation of any unintended ORFs in a silencing construct will be halted as for any placement of ALLSTOPS. In addition, it may be expected that siRNAs to the ALLSTOPS sequences will be generated by DICER, or DICER-LIKE. Any siRNAs produced may act to trigger the RISC-mediated degradation of any transcript that contains the ALLSTOPS sequence. In this way, unintended transcripts will be degraded even before any translation occurs.

Example 2

Any transformation method can be used to deliver an ALLSTOPS containing polynucleotide to any appropriate cell, organism, or tissue target. DNA constructs for transformation comprising ALLSTOPS are produced using standard molecular biological techniques.

A. Particle Bombardment of Maize

Immature maize embryos from greenhouse or field grown High type II (Hill) donor plants are bombarded with an isolated polynucleotide comprising an ALLSTOPs polynucleotide. If the polynucleotide does not include a selectable marker, another polynucleotide containing a selectable marker gene can be co-precipitated on the particles used for bombardment. For example, a plasmid containing the PAT gene (Wohlleben, et al., (1988) *Gene* 70:25-37) which confers resistance to the herbicide Bialaphos can be used. Transformation is performed as follows.

The ears are surface sterilized in 50% Chlorox bleach plus 0.5% Micro detergent for 20 minutes, and rinsed two times with sterile water. Immature embryos are excised and placed embryo axis side down (scutellum side up), 25 embryos per plate. These are cultured in the dark on 560L agar medium 4 days prior to bombardment. Medium 560L is an N6-based medium containing Eriksson's vitamins, thiamine, sucrose, 2,4-D, and silver nitrate. The day of bombardment, the embryos are transferred to 560Y medium for 4 hours and are arranged within a 2.5-cm target zone. Medium 560Y is a high osmoticum medium (560L with high sucrose concentration).

A circular or linear DNA construct comprising an ALLSTOPS sequence, and optionally a polynucleotide of interest operably linked to a promoter, is constructed. This DNA construct, optionally plus a DNA construct containing a PAT selectable marker if needed, is precipitated onto 1.0 µm (average diameter) gold pellets using a $CaCl_2$ precipitation procedure as follows: 100 µprepared gold particles (0.6 mg) in water, 20 µl (2 µg) DNA in TrisEDTA buffer (1 µg total), 100 µl 2.5 M $CaCl_2$, 40 µl 0.1 M spermidine.

Each reagent is added sequentially to the gold particle suspension. The final mixture is sonicated briefly. After the precipitation period, the tubes are centrifuged briefly, liquid removed, washed with 500 µl 100% ethanol, and centrifuged again for 30 seconds. Again the liquid is removed, and 60 µl 100% ethanol is added to the final gold particle pellet. For particle gun bombardment, the gold/DNA particles are briefly sonicated and 5 µl spotted onto the center of each macrocarrier and allowed to dry about 2 minutes before bombardment.

The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Four to 12 hours post bombardment, the embryos are moved to a low osmoticum callus initiation medium for 3-7 days, then transferred to selection medium 3 mg/liter Bialaphos, and subcultured every 2 weeks. After approximately 10 weeks of selection, callus clones are sampled for PCR and/or activity of the polynucleotide of interest. Positive lines are transferred to regeneration medium to initiate plant regeneration. Following somatic embryo maturation (2-4 weeks), well-developed somatic embryos are transferred to medium for germination and transferred to a lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the polynucleotide of interest.

B. *Agrobacterium*-Mediated Transformation of Maize

For *Agrobacterium*-mediated transformation of maize, a polynucleotide comprising a recombination site, transfer cassette, target site, and/or recombinase provided herein is used with the method of Zhao (U.S. Pat. No. 5,981,840).

Briefly, immature embryos are isolated from maize and the embryos contacted with a suspension of *Agrobacterium* containing a polynucleotide of interest, where the bacteria are capable of transferring the nucleotide sequence of interest to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). Following this co-cultivation period an optional "resting" step may be performed (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

C. Particle Bombardment Transformation of Soy

A polynucleotide comprising an ALLSTOPS polynucleotide, and optionally a polynucleotide of interest operably linked to a promoter, can be introduced into embryogenic suspension cultures of soybean by particle bombardment using essentially the methods described in Parrott, et al., (1989) *Plant Cell Rep* 7:615-617. This method, with modifications, is described below.

Seed is removed from pods when the cotyledons are between 3 and 5 mm in length. The seeds are sterilized in a bleach solution (0.5%) for 15 minutes after which time the seeds are rinsed with sterile distilled water. The immature cotyledons are excised by first cutting away the portion of the seed that contains the embryo axis. The cotyledons are then removed from the seed coat by gently pushing the distal end of the seed with the blunt end of the scalpel blade. The cotyledons are then placed in Petri dishes (flat side up) with SB1 initiation medium (MS salts, B5 vitamins, 20 mg/L 2,4-D, 31.5 g/L sucrose, 8 g/L TC Agar, pH 5.8). The Petri plates are incubated in the light (16 hr day; 75-80 µE) at 26° C. After 4 weeks of incubation the cotyledons are transferred to fresh SB1 medium. After an additional two weeks, globular stage somatic embryos that exhibit proliferative areas are excised and transferred to FN Lite liquid medium (Samoylov, et al., (1998) *In Vitro Cell Dev Biol Plant* 34:8-13). About 10 to 12 small clusters of somatic embryos are placed in 250 ml flasks containing 35 ml of SB172 medium. The soybean embryogenic suspension cultures are maintained in 35 mL liquid media on a rotary shaker, 150 rpm, at 26° C. with florescent lights (20 µE) on a 16:8 hour day/night schedule. Cultures are sub-cultured every two weeks by inoculating approximately 35 mg of tissue into 35 mL of liquid medium.

Soybean embryogenic suspension cultures are then transformed using particle gun bombardment (e.g., Klein, et al., (1987) *Nature* 327:70; U.S. Pat. No. 4,945,050). A BioRad Biolisticä PDS1000/HE instrument can be used for these transformations. A selectable marker gene, which is used to facilitate soybean transformation, is a chimeric gene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is agitated for three minutes, spun in a microfuge for 10 seconds and the supernatant removed. The DNA-coated particles are washed once in 400 µL 70% ethanol and resuspended in 40 µL of anhydrous ethanol. The DNA/particle suspension is sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. Membrane rupture pressure is set at 1100 psi and the chamber is evacuated to a vacuum of 28 inches mercury. The tissue is placed approximately 8 cm away from the retaining screen, and is bombarded three times. Following bombardment, the tissue is divided in half and placed back into 35 ml of FN Lite medium.

Five to seven days after bombardment, the liquid medium is exchanged with fresh medium. Eleven days post bombardment the medium is exchanged with fresh medium containing 50 mg/mL hygromycin. This selective medium is refreshed weekly. Seven to eight weeks post bombardment, green, transformed tissue will be observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos, or tissue is regenerated into whole plants by maturation and germination of individual embryos.

D. DNA Isolation from Plant Callus or Leaf Tissues

Putative transformation events can be screened for the presence of a transgene. Genomic DNA is extracted from calli or leaves using a modification of the CTAB (cetyltriethylammonium bromide, Sigma H5882) method described by Stacey and Isaac (1994) In *Methods in Molecular Biology* Vol. 28, pp. 9-15, Ed. P. G. Isaac, Humana Press, Totowa, N.J. Approximately 100-200 mg of frozen tissue is ground into powder in liquid nitrogen and homogenized in 1 ml of CTAB extraction buffer (2% CTAB, 0.02 M EDTA, 0.1 M Tris-Cl pH 8, 1.4 M NaCl, 25 mM DTT) for 30 min at 65° C. Homogenized samples are allowed to cool at room temperature for 15 min before a single protein extraction with approximately 1 ml 24:1 v/v chloroform:octanol is done. Samples are centrifuged for 7 min at 13,000 rpm and the upper layer of supernatant collected using wide-mouthed pipette tips. DNA is precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five µl RNAse A is added to the samples and incubated at 37° C. for 1 h. For quantification of genomic DNA, gel electrophoresis is performed using a 0.8% agarose gel in 1× TBE buffer. One microliter of each of the samples is fractionated alongside 200, 400, 600 and 800 ng µl-1 λ uncut DNA markers.

E. Transformation of Bacterial Cells

The ALLSTOPS sequences provided herein can also be evaluated and used in bacterial cells, such as *Agrobacterium* or *E. coli*. Many commercially available competent cell lines and bacterial plasmids are well known and readily available. Isolated polynucleotides for transformation and transformation of bacterial cells can be done by any method known in the art. For example, methods of *E. coli* and other bacterial cell transformation, plasmid preparation, and the use of phages are detailed, for example, in *Current Protocols in Molecular Biology* (Ausubel, et al., (eds.) (1994) a joint venture between Greene Publishing Associates, Inc. and John Wiley & Sons, Inc.). For example, an efficient electroporation protocol (Tung and Chow, *Current Protocols in Molecular Biology*, Supplement 32, Fall 1995) is summarized below.

Inoculate 100 ml LB medium with 1 ml *E. coli* overnight culture. Incubate at 37° C. with vigorous shaking until culture reached OD600=0.6. Chill culture on ice 30 min., then pellet cells by centrifuging 4,000×g for 15 min at 4° C. Wash cell pellet twice with 50 ml ice-cold 10% glycerol. After final wash, resuspend cell pellet to a final volume of 0.2 ml in ice-cold GYT medium (10% v/v glycerol; 0.125% w/v yeast extract; 0.25% w/v tryptone). Electroporate in prechilled cuvettes using manufacturer's conditions, for example 0.5 ng plasmid DNA/transformation using Gene Pulser (BioRad) set to 25 µF, 200 ohms, 2.5 kV. Immediately after electroporation, add 1 ml SOC medium and transfer cells to a culture tube. Incubate at 37° C. for 1 hr. Plate aliquots of cells on selective agar plates and incubate overnight at 37° C. Pick resistant colonies and archive or grow to confirm DNA delivery and characterization of events. DNA can be isolated and analyzed from putative transformed lines using any standard procedures, including commercially available kits.

F. Transformation of Yeast

The ALLSTOPS sequences provided herein can also be evaluated and used in yeast cells. Many commercially and/or publicly available strains of *S. cerevisiae* are available, as are plasmids used to transform these cells. For example, strains are available from the American Type Culture Collection (ATCC, Manassas, Va.) and includes the Yeast Genetic Stock Center inventory, which moved to the ATCC in 1998. Other yeast lines, such as *S. pombe* and *P. pastoris*, and the like are also available. Methods of yeast transformation, plasmid preparation, and the like are detailed, for example, in *Current Protocols in Molecular Biology* (Ausubel, et al., (eds.) (1994) a joint venture between Greene Publishing Associates, Inc. and John Wiley & Sons, Inc., see Unit 13 in particular). Transformation methods for yeast include spheroplast transformation, electroporation, and lithium acetate methods. A versatile, high efficiency transformation method for yeast is described by Gietz and Woods ((2002) *Methods Enzymol* 350:87-96) using lithium acetate, PEG 3500 and carrier DNA.

G. Transformation of Mammalian Cells

The ALLSTOPS sequences provided herein can also be evaluated and used in mammalian cells, such as CHO, HeLa, BALB/c, fibroblasts, mouse embryonic stem cells and the like. Many commercially available competent cell lines and plasmids are well known and readily available, for example from the ATCC (Manassas, Va.). Isolated polynucleotides for transformation and transformation of mammalian cells can be done by any standard method. For example, methods of mammalian and other eukaryotic cell transformation, plasmid preparation, and the use of viruses are detailed, for example, in *Current Protocols in Molecular Biology* (Ausubel, et al., (eds.) (1994) a joint venture between Greene Publishing Associates, Inc. and John Wiley & Sons, Inc., see, Unit 9, in particular). For example, many methods are available, such as calcium phosphate transfection, electoporation, DEAE-dextran transfection, liposome-mediated transfection, and microinjection, as well as viral techniques.

Example 3

The functionality of an ALLSTOPS polynucleotide can be confirmed in variety of ways. In one example a single vector is constructed for plant transformation wherein the construct has two expression cassettes: 1) ubi pro driving an inverted repeat of phytoene desaturase (PDS) with ALLSTOPS incorporated into each arm; and 2) H2B pro driving DS-RED with ALLSTOPS added just after or in place of the natural stop codon as a 3' tag.

Control vectors for plant transformation are 1) ALLSTOPS-tagged DS-RED cassette paired with untagged PDS, and; 2) ALLSTOPS-tagged DS-RED paired with PDS tagged with something other than ALLSTOPS.

Plantlets transformed with the ALLSTOPS test construct should have the following phenotypes:

green plantlets should be RFP+; and, white/bleached plantlets should be RFP−.

Plantlets transformed with the control vectors should all be RFP+ regardless of green/white phenotype.

Transient transformation can also be used to assay for ALLSTOPS function. In one example, constructs are designed which encode a fusion protein with a GFP reporter with and without an intervening ALLSTOPS in the linker region:

PRO::GUS-linker-GFP::term; and,

PRO::GUS-ALLSTOPS-GFP::term.

Transient transformation of *E. coli*, or other host cells, can be used to measure the relative expression of GUS and GFP from the construct with an intervening linker region as compared to the construct having the ALLSTOPS linker.

What is claimed is:

1. A recombinant T-DNA expression cassette comprising the polynucleotide of SEQ ID NO: 7, wherein the polynucleotide is inserted flanking both ends of the recombinant T-DNA expression cassette and wherein the polynucleotide truncates translation of unintended mRNA transcripts.

2. The recombinant T-DNA expression cassette of claim 1, wherein the polynucleotide is inserted 3' or 5' of a T-DNA left border and 3' or 5' of a T-DNA right border.

* * * * *

SEQUENCE LISTING

<160> NUMBER OF SEQ ID NOS: 15

<210> SEQ ID NO 1
<211> LENGTH: 34
<212> TYPE: DNA
<213> ORGANISM: Artificial Sequence
<220> FEATURE:
<223> OTHER INFORMATION: Synthetic sequence

<400> SEQUENCE: 1
taagtgacta gggtcacgtg accctagtca ctta					34

<210> SEQ ID NO 2
<211> LENGTH: 12
<212> TYPE: DNA
<213> ORGANISM: Artificial Sequence
<220> FEATURE:
<223> OTHER INFORMATION: Synthetic sequence

<400> SEQUENCE: 2
ctagctagtt ag					12

<210> SEQ ID NO 3
<211> LENGTH: 12
<212> TYPE: DNA
<213> ORGANISM: Artificial Sequence
<220> FEATURE:
<223> OTHER INFORMATION: Synthetic sequence

<400> SEQUENCE: 3
ctaactaact aa					12

<210> SEQ ID NO 4
<211> LENGTH: 21
<212> TYPE: DNA
<213> ORGANISM: Artificial Sequence
<220> FEATURE:
<223> OTHER INFORMATION: Synthetic sequence

<400> SEQUENCE: 4
ctgatcacta gttacttata g					21

<210> SEQ ID NO 5
<211> LENGTH: 17
<212> TYPE: DNA
<213> ORGANISM: Artificial Sequence
<220> FEATURE:
<223> OTHER INFORMATION: Synthetic sequence

<400> SEQUENCE: 5
tagtcactga ttagtca					17

<210> SEQ ID NO 6
<211> LENGTH: 28
<212> TYPE: DNA
<213> ORGANISM: Artificial Sequence
<220> FEATURE:
<223> OTHER INFORMATION: Synthetic sequence

<400> SEQUENCE: 6
tgacgtgtaa gccgtagtta cctagtca					28

<210> SEQ ID NO 7
<211> LENGTH: 12
<212> TYPE: DNA

```
<213> ORGANISM: Artificial Sequence
<220> FEATURE:
<223> OTHER INFORMATION: Synthetic sequence

<400> SEQUENCE: 7
ctaactaact ag                                                             12

<210> SEQ ID NO 8
<211> LENGTH: 36
<212> TYPE: DNA
<213> ORGANISM: Artificial Sequence
<220> FEATURE:
<223> OTHER INFORMATION: Synthetic oligonucleotide RB1

<400> SEQUENCE: 8
tactaccggt taagtgacta gggtcacgtg acccta                                    36

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide RB2

<400> SEQUENCE: 9
tgaccctagt cacttaaccg gtagtaac                                             28

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide RB3

<400> SEQUENCE: 10
gtcacttagg ttaccagagc t                                                    21

<210> SEQ ID NO 11
<211> LENGTH: 37
<212> TYPE: DNA
<213> ORGANISM: Artificial Sequence
<220> FEATURE:
<223> OTHER INFORMATION: Synthetic oligonucleotide RB4

<400> SEQUENCE: 11
gtgaccagct ctggtaacct aagtgactag ggtcacg                                   37

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide LB5

<400> SEQUENCE: 12
cggtacctaa gtgactaggg tcacgtg                                              27

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide LB6

<400> SEQUENCE: 13
agtcacttag gtaccgagct                                                     20
```

-continued

```
<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide LB7

<400> SEQUENCE: 14
accctagtca cttatc                                                 16

<210> SEQ ID NO 15
<211> LENGTH: 31
<212> TYPE: DNA
<213> ORGANISM: Artificial Sequence
<220> FEATURE:
<223> OTHER INFORMATION: Synthetic oligonucleotide LB8

<400> SEQUENCE: 15
ggccgataag tgactagggt cacgtgaccc t                                31
```